United States Patent
Ito et al.

(10) Patent No.: US 10,736,941 B2
(45) Date of Patent: Aug. 11, 2020

(54) CELL MEMBRANE-PERMEATING PEPTIDE

(71) Applicant: NATIONAL UNIVERSITY CORPORATION KUMAMOTO UNIVERSITY, Kumamoto-shi, Kumamoto (JP)

(72) Inventors: Shingo Ito, Kumamoto (JP); Sumio Ohtsuki, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 15/575,331

(22) PCT Filed: May 18, 2016

(86) PCT No.: PCT/JP2016/064767
§ 371 (c)(1),
(2) Date: Oct. 24, 2018

(87) PCT Pub. No.: WO2016/186140
PCT Pub. Date: Nov. 24, 2016

(65) Prior Publication Data
US 2019/0054148 A1 Feb. 21, 2019

(30) Foreign Application Priority Data

May 19, 2015 (JP) ................................ 2015-101497

(51) Int. Cl.
| | | |
|---|---|---|
| A61K 38/28 | (2006.01) | |
| A61K 47/40 | (2006.01) | |
| A61K 9/127 | (2006.01) | |
| A61K 31/711 | (2006.01) | |
| A61K 31/713 | (2006.01) | |
| C07K 7/06 | (2006.01) | |
| C12N 7/00 | (2006.01) | |
| A61K 45/06 | (2006.01) | |
| C07K 7/64 | (2006.01) | |
| C07K 19/00 | (2006.01) | |
| C12N 15/113 | (2010.01) | |
| A61P 3/10 | (2006.01) | |

(52) U.S. Cl.
CPC ............. *A61K 38/28* (2013.01); *A61K 9/127* (2013.01); *A61K 31/711* (2013.01); *A61K 31/713* (2013.01); *A61K 45/06* (2013.01); *A61K 47/40* (2013.01); *A61P 3/10* (2018.01); *C07K 7/06* (2013.01); *C07K 7/64* (2013.01); *C07K 19/00* (2013.01); *C12N 7/00* (2013.01); *C12N 15/113* (2013.01); *C12N 2795/14121* (2013.01); *C12N 2795/14131* (2013.01)

(58) Field of Classification Search
None
See application file for complete search history.

(56) References Cited

FOREIGN PATENT DOCUMENTS

| | | | |
|---|---|---|---|
| JP | 2006304619 A | | 11/2006 |
| JP | 2010100781 A | | 5/2010 |
| WO | WO2007-146359 | * | 1/2007 |
| WO | WO2010-0096838 | * | 1/2010 |

OTHER PUBLICATIONS

NCBI Reference Sequence: WP_090619034.1(Jan. 12, 2018).*
UniProtKB-Q92547 (TOPB1_Human) <https://www.uniprot.org/uniprot/Q92547>integrated into UniProtKB Apr. 26, 2005).*
NCBI Reference Sequence: XM_006261943.1 (<https://www.ncbi.nlm.nih.gov/nuccore/XM_006261943.1> entered into publix database:Dec. 9, 2013).*
Liu et al. ("Regulation of TopBP1 oligomerization by Akt/PKB for cell survival" The EMBO Journal (2006) 25, 4795-4807).*
Joo et al. ("Cyclic Peptides as Therapeutic Agents and Biochemical Tools" Biomol Ther (Seoul) Jan. 2012; 20(1):19-26 and Stagliano et al. (WO 2010/0096838).*
LifeTein Peptide Synthesis (<https://www.lifetein.com/Peptide-Synthesis-D-Amino-Acid.html> May 12, 2012).*
Akbarzadeh et al. ("Liposome: classification, preparation, and applications" Nanoscale Res Lett. 2013;8(1):102).*
Takeuchi, H. et al., "Mucoadhesive Properties of Carbopol of Chitosan-coated liposomes and their Effectiveness in the Oral Administration of Calcitonin to rats," Journal of Controlled Release, vol. 86, pp. 235-242, 2003.
Agarwal, Vikas et al., "Polymethyacryiete based Microparticulates of insulin for oral delivery: Preparation and in vitro dissolution stability in the presence of enzyme Inhibitors," International Journal of Pharmaceutics, vol. 225, pp. 31-39, 2001.
Morishita, Mariko et al., "Mucosal insulin delivery Systems based on Complexation Polymer hydrogels: Effects of Particle size on insulin Enteral Absorption," Journal of Controlled Release, vol. 97, pp. 115-124, 2004.

(Continued)

*Primary Examiner* — James H Alstrum-Acevedo
*Assistant Examiner* — Tara L Martinez
(74) *Attorney, Agent, or Firm* — Hunton Andrews Kurth LLP

(57) ABSTRACT

The present invention addresses to provide a novel membrane permeability-improving agent which can be applied to high molecular drugs. More specifically, the present invention addresses to provide: a drug carrier which can improve the absorption efficiency of a high molecular drug in the small intestine; and a membrane permeation-improving agent containing the carrier. According to the present invention, a cell membrane-permeating peptide can be provided, which comprises an amino acid sequence selected from the group consisting of the following amino acid sequences: DNPGN (SEQ ID NO: 1); SRPAF (SEQ ID NO: 2); NDPRN (SEQ ID NO: 3); and MSVAN (SEQ ID NO: 4). According to the present invention, a cell membrane-permeable composition can also be provided, which comprises the peptide and a biologically active substance.

18 Claims, 3 Drawing Sheets

Specification includes a Sequence Listing.

(56) References Cited

OTHER PUBLICATIONS

Yamamoto, A "Promotion of Transmucosal Permeation of Peptide and protein drugs," Yakuzaigaku, vol. 74, No. 1 pp. 19-26, 2014.
Akira Yamamoto, "Improvement of Transmucosal Delivery of Peptide and Protein Drugs", 2014, Journal of Pharmaceutical Science and Technology, Japan, vol. 74, No. 1, pp. 19 to 26, p. 22, right column, 2nd paragraph.
Ohura K, et al., "Evaluation of Transport Mechanism of Prodrugs and Parent Drugs Formed by Intracellular Metabolism in Caco-2 Cells with Modified Carboxylesterase Activity:" Temocapril as a Model Case, 2011, Journal of Pharmaceutical Sciences, vol. IOO, No. 9, p. 3985-3994, p. 3986, right column, 2nd paragraph to p. 3988, left column, 1st paragraph.
International Search Report for PCT application No. PCT/JP2016/064767, dated Jun. 21, 2016.

\* cited by examiner

Fig. 7
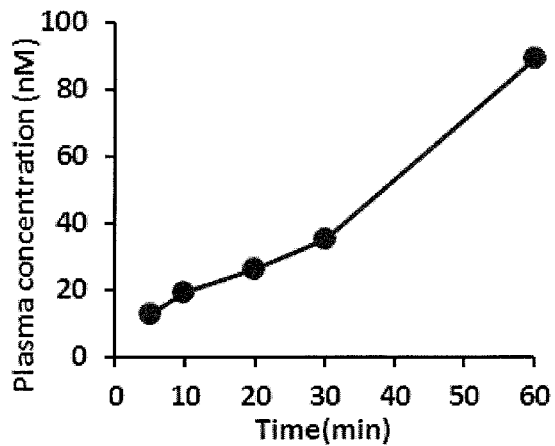
Fig. 8
M-coffee alignment result
| | Amino Acid Sequence | Score |
|---|---|---|
| SEQ ID No: 9 | D N P G N E T | 82 |
| SEQ ID No: 10 | T V S R P A F | 87 |
| SEQ ID No: 11 | H S N D P R N | 82 |
| SEQ ID No: 12 | P F M S V A N | 73 |
Fig. 9
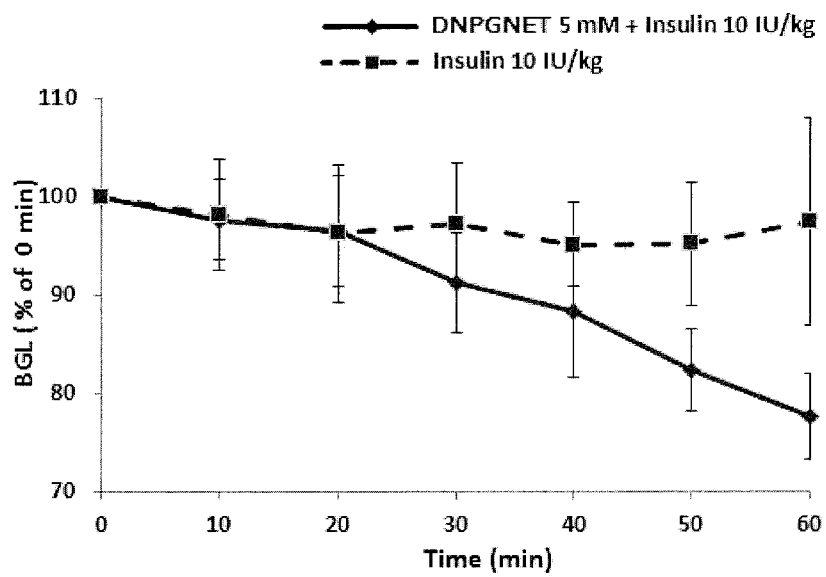

```
SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: identified using phage display

<400> SEQUENCE: 1

Asp Asn Pro Gly Asn
1               5

<210> SEQ ID NO 2
<211> LENGTH: 5
<212> TYPE: PRT
<213> ORGANISM: Artificial Sequence
<220> FEATURE:
<223> OTHER INFORMATION: identified using phage display

<400> SEQUENCE: 2

Ser Arg Pro Ala Phe
1               5

<210> SEQ ID NO 3
<211> LENGTH: 5
<212> TYPE: PRT
<213> ORGANISM: Artificial Sequence
<220> FEATURE:
<223> OTHER INFORMATION: identified using phage display
```

```
<400> SEQUENCE: 3

Asn Asp Pro Arg Asn
1               5

<210> SEQ ID NO 4
<211> LENGTH: 5
<212> TYPE: PRT
<213> ORGANISM: Artificial Sequence
<220> FEATURE:
<223> OTHER INFORMATION: identified using phage display

<400> SEQUENCE: 4

Met Ser Val Ala Asn
1               5

<210> SEQ ID NO 5
<211> LENGTH: 7
<212> TYPE: PRT
<213> ORGANISM: Artificial Sequence
<220> FEATURE:
<223> OTHER INFORMATION: identified using phage display

<400> SEQUENCE: 5

Asp Asn Pro Gly Asn Glu Thr
1               5

<210> SEQ ID NO 6
<211> LENGTH: 7
<212> TYPE: PRT
<213> ORGANISM: Artificial Sequence
<220> FEATURE:
<223> OTHER INFORMATION: identified using phage display

<400> SEQUENCE: 6

Thr Val Ser Arg Pro Ala Phe
1               5

<210> SEQ ID NO 7
<211> LENGTH: 7
<212> TYPE: PRT
<213> ORGANISM: Artificial Sequence
<220> FEATURE:
<223> OTHER INFORMATION: identified using phage display

<400> SEQUENCE: 7

His Ser Asn Asp Pro Arg Asn
1               5

<210> SEQ ID NO 8
<211> LENGTH: 7
<212> TYPE: PRT
<213> ORGANISM: Artificial Sequence
<220> FEATURE:
<223> OTHER INFORMATION: identified using phage display

<400> SEQUENCE: 8

Pro Phe Met Ser Val Ala Asn
1               5

<210> SEQ ID NO 9
<211> LENGTH: 6
<212> TYPE: PRT
<213> ORGANISM: Artificial Sequence
<220> FEATURE:
<223> OTHER INFORMATION: identified using phage display
```

```
<400> SEQUENCE: 9

Asp Asn Pro Gly Asn Glu
1               5
```

CELL MEMBRANE-PERMEATING PEPTIDE

TECHNICAL FIELD

The present invention relates to a novel cell membrane-permeable peptide.

BACKGROUND ART

Oral administration is a method by which a medicinal product can be taken relatively safely since a medicine can be taken naturally and simply in daily lives by oral administration and it is non-invasive. Since the digestive tract has a structure suitable for drug absorption and has large absorption surface area, development of an oral preparation as the medicinal preparation is desired. However, there are some problems which should be overcome for enabling oral administration of a drug.

One problem is possibility of degradation of a drug by enzymes in the digestive tract before migration into the general circulation. For solving this, deactivation of a drug in stomach can be prevented by an enteric-coated preparation technology or the like, thereby delivering the drug into the intestinal tract.

Another problem is insufficient permeation of a drug through the intestinal tract mucosal epithelium. Absorbability in the digestive tract is one important determination factor of the pharmacokinetics and the pharmacological activity of a medicinal product in oral administration. However, since a water-soluble high molecular medicinal product such as nucleic acids expected as the next-generation medicinal product shows extremely low digestive tract absorbability, administration thereof is limited to an intravenous injection method rather than oral administration, in clinical practice.

Studies using absorption promoters and additives for transiently increasing the substance permeability of a biological membrane have been conducted to date, for attaining an improvement in the absorbability of a medicinal product by the digestive tract. The absorption promoter includes surfactants, fatty acids and alcohols. The absorption promoters and the additives, however, have safety issues that absorption by the digestive tract is increased non-specifically by opening and closing of tight junction, the effect cannot be exhibited sufficiently because of dilution with water or the like in a biological body, mucous membrane disorders occur in the local, and the like. Therefore, the practical use thereof is limited to a suppository. These methods are insufficient for an improvement in the absorption efficiency of a high molecular medicinal product even if the methods can be applied to an improvement in the absorption efficiency of a low molecular medicinal product.

Further, studies of increasing absorption in the digestive tract using cell membrane-permeable peptides such as human immunodeficiency virus (HIV)-1 Tat peptide, HIV-1 Lev peptide, penetratin, transportan and arginine oligomer have also been conducted. There are peptides promoting absorption of insulin from the digestive tract in basic studies, however, its efficiency is still about 20% and there is no clinically applied peptide, thus, further efficient sequences are sought.

Furthermore, there is suggested also a transepithelial absorption promoter in which absorption of a coexistent drug is improved by binding a cell membrane-permeable peptide to a backbone polymer as a base material (Patent document 1).

In addition, a chitosan-modified liposome is developed (Non-Patent document 1). Its transport mechanism is mainly composed of permeation through intercellular gap, acting on F-actin, to weaken tight junction. However, transcellular transport is also said to be adsorptive endocytosis via mutual interaction with mucin. This is not yet clinically applied, too.

As a method of improving small-intestinal absorption of a high molecular medicinal product, a method combining a protease inhibitor and a drug carrier is suggested (Non-Patent document 2). In this method, degradation of insulin as a peptide/protein preparation can be suppressed 100% by a protease inhibitor. It is reported that bioavailability in rat oral administration is improved up to 10% by enclosing insulin in smart hydrogel as a drug carrier (Non-Patent document 3). The drug reaches small intestine, however, its absorption rate is not sufficient yet.

For this reason, a further excellent drug carrier which can be administered orally and intending an improvement in absorption in small intestine has been desired.

CITED LIST

Patent Document

Patent Document 1: Japanese Unexamined Patent Application Publication No. 2008-275729

Non-Patent Document

Non-Patent Document 1: J Control Release. 2003 Jan. 17; 86(2-3):235-42
Non-Patent Document 2: Int J Pharm. 2001 Aug. 28; 225 (1-2):31-9
Non-Patent Document 3: Journal of Controlled Release 97(2004)115-124

SUMMARY OF THE INVENTION

Technical Problem

The present invention has an object of providing a novel membrane permeability-improving agent applicable also to a high molecular medicinal product. More specifically, it is intended to provide a drug carrier which can improve efficiency of absorption of a high molecular drug in small intestine and a membrane permeability-improving agent containing the carrier.

Solution to Problem

The present inventors have intensively studied to solve the above-described problems and resultantly found that a high molecule having a short peptide containing a specific amino acid sequence is small intestine-permeable, leading to completion of the present invention.

The present invention includes the followings.
[1] A cell membrane-permeable peptide comprising an amino acid sequence selected from the group consisting of the following amino acid sequences: DNPGN (SEQ ID No: 1), SRPAF (SEQ ID No: 2), NDPRN (SEQ ID No: 3) and MSVAN (SEQ ID No: 4).
[2] The cell membrane-permeable peptide according to [1], wherein the peptide comprises at least one unnatural amino acid.
[3] The cell membrane-permeable peptide according to [1] or [2], wherein the peptide comprises an amino acid sequence selected from the group consisting of amino acid sequences: DNPGNET (SEQ ID No: 5), TVSRPAF (SEQ ID No: 6), HSNDPRN (SEQ ID No: 7) and PFMSVAN (SEQ ID No: 8).

[4] The cell membrane-permeable peptide according to [1] or [2], wherein the peptide comprises an amino acid sequence of DNPGN (SEQ ID No: 1) or DNPGNE (SEQ ID No: 9).

[5] The cell membrane-permeable peptide according to any one of [1] to [4], wherein the peptide is a cyclic peptide.

[6] The cell membrane-permeable peptide according to [5], wherein the cyclic peptide contains a Cys-Cys disulfide bond.

[7] The cell membrane-permeable peptide according to any one of [1] to [6], wherein the peptide permeates small intestine epithelial cells of mammals.

[8] A cell membrane-permeable composition comprising a peptide comprising an amino acid sequence selected from the group consisting of the following amino acid sequences: DNPGN (SEQ ID No: 1), SRPAF (SEQ 11) No: 2), NDPRN (SEQ ID No: 3) and MSVAN (SEQ ID No: 4), and a biologically active substance, wherein the peptide binds to or forms a complex with the biologically active substance or an active substance carrier containing the biologically active substance.

[9] The composition according to [8], wherein the peptide comprises at least one unnatural amino acid.

[10] The composition according to [8] or [9], wherein the peptide comprises an amino acid sequence selected from the group consisting of amino acid sequences: DNPGNET (SEQ ID No: 5), TVSRPAF (SEQ ID No: 6), HSNDPRN (SEQ ID No: 7) and PFMSVAN (SEQ ID No: 8).

[11] The composition according to [8] or [9], wherein the peptide comprises an amino acid sequence of DNPGN (SEQ ID No: 1) or DNPGNE (SEQ ID No: 9).

[12] The composition according to any one of [8] to [11], wherein the peptide is a cyclic peptide.

[13] The composition according to [12], wherein the cyclic peptide contains a Cys-Cys disulfide bond.

[14] The composition according to any one of [8] to [13], wherein the biologically active substance comprises a high molecule.

[15] The composition according to [14], wherein the high molecule comprises a biologically active peptide or a protein.

[16] The composition according to [15], wherein the biologically active peptide is insulin.

[17] The composition according to [14], wherein the high molecule contains nucleic acids.

[18] The composition according to [17], wherein the nucleic acids is antisense DNA, siRNA or shRNA.

[19] The composition according to any one of [8] to [18], wherein the active substance carrier containing the biologically active substance is a liposome.

[20] The composition according to any one of [8] to [18], wherein the active substance carrier containing the biologically active substance is a cyclodextrin.

Advantageous Effect of the Invention

According to the present invention, a novel cell membrane-permeable peptide which efficiently permeates small intestine as the main tissue of digestive tract absorption is provided. Further, according to the present invention, a cell membrane-permeable peptide which can transport a high molecule efficiently to small intestine epithelial cells and a high molecular medicinal product containing the peptide can be provided.

BRIEF DESCRIPTION OF DRAWINGS

FIG. 7 shows the result of small intestine permeability of a synthetic FAM-labeled DNP peptide, by an in situ closed loop method using a digestive tract loop of an ICR mouse.

FIG. 8 shows the results of alignment analysis of four peptides identified, using an M-Coffe web server.

FIG. 9 shows the results of insulin absorption by co-administration of the cyclic DNP peptide of the present invention, confirmed by measuring the blood glucose level.

DESCRIPTION OF EMBODIMENTS

Figure 1:
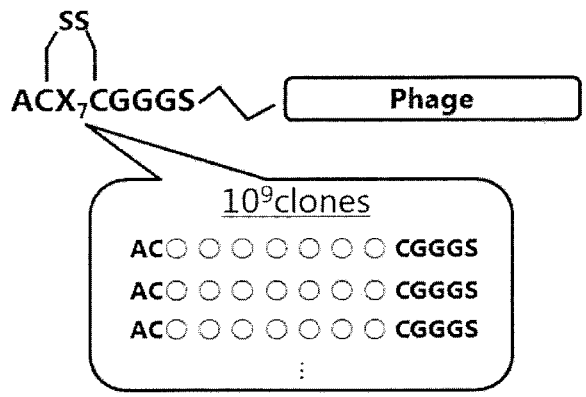
FIG. 1 shows a cyclic amino acid structure displayed in a phage.

The present invention will be illustrated below referring to exemplary embodiments, together with preferable methods and materials which can be used in carrying out the invention. All technical terms and scientific terms used in the present specification have the same meanings as those generally understood by the person skilled in the art to which the present invention pertains, unless otherwise stated in the sentence. Optional materials and methods which are equivalent to or the same as those described in the present specification can be used in the same manner in carrying out the present invention.

Further, all published materials and patents cited in the present specification in association with the invention described in the present specification constitute parts of the present specification, as those showing methods, materials and other matters which can be used in the present invention.

(1) Cell Membrane-Permeable Peptide

In the present invention, the cell membrane-permeable peptide includes L-configured or D-configured peptides having an amino acid sequence of DNPGN, SRPAF, NDPRN or MSVAN. In addition to amino acids having L steric configuration which are naturally present amino acids, unnatural amino acids such as a derivative obtained by partially modifying the structure of a natural amino acid can also be used. The unnatural amino acid is not particularly restricted, and any known amino acids can be used. For example, amino acids having D steric configuration and N-methyl-amino acid can be effectively used in the peptide of the present invention since they hardly undergo degradation by a protease. In the peptide of the present invention, at least a part of its amino acid sequence may be an unnatural amino acid such as D amino acids and N-methylamino acids.

The cell membrane-permeable peptide of the present invention is a cell membrane-permeable peptide containing an amino acid sequence of DNPGN (SEQ ID No: 1), SRPAF (SEQ ID No: 2), NDPRN (SEQ ID No: 3) or MSVAN (SEQ TD No: 4), preferably a peptide containing an amino acid sequence of DNPGN, DNPGNE (SEQ ID No: 9), DNPG-NET (SEQ ID No: 5), TVSRPAF (SEQ ID No: 6), HSND-PRN (SEQ ID No: 7) or PFMSVAN (SEQ ID No: 8), more preferably a peptide containing an amino acid sequence of DNPGN, DNPGNE or DNPGNET.

In the present invention, the cell membrane-permeable peptide has a meaning including a peptide of L amino acids or D amino acids represented by the above-described sequences or a peptide obtained by mixing them, and its reverse peptide. For example, the peptide containing an amino acid sequence DNPGN has a meaning including both a peptide containing sequences thereof in the order of (N-terminal)-DNPGN-(C-terminal) and a peptide containing sequences thereof in the order of (N-terminal)-NGPND-(C-terminal).

"Having an amino acid sequence" described above may be having an amino acid sequence solely composed of the above-described sequence, for example, 5 amino acid sequences represented by DNPGN, or may be optionally having amino acid(s) at each of the C-terminal side and/or N-terminal side of an amino acid sequence having the above-described sequence or having one or several amino acids in total, preferably independently 1 to 4 amino acids.

When amino acid(s) are optionally contained at the C-terminal side and/or N-terminal side of an amino acid sequence having the above-described sequence, a peptide portion composed of the above-described sequence may be a reverse peptide sequence. For example, in the case of an amino acid sequence of DNPGN, for example, having one amino acid at the C terminal side of an amino acid sequence may denote (N-terminal)-DNPGNX-(C-terminal) (X represents any amino acid) or (N-terminal)-NGPNDX-(C-terminal) (X represents any amino acid).

The cell membrane-permeable peptide of the present invention can transport a high molecule including, but not limited to, for example, a biologically active peptide, a protein or nucleic acids into a cell, preferably into a cell of small intestine, by having the above-described sequence.

The peptide of the present invention can be produced according to a known peptide synthesis method. The cell membrane-permeable peptide of the present invention of which at least a part of the peptide is composed of an unnatural amino acid can be produced, by using as the material an unnatural amino acid in addition to a natural amino acid. Examples thereof include peptides partially composed of a D amino acid or an N-methylated amino acid. The peptide synthesis method includes, for example, solid phase synthesis methods, liquid phase synthesis methods and the like, and after the synthesis reaction, the peptide of the present invention can be isolated and purified by using purification methods usually used in the field of peptides, for example, technologies such as extraction with solvents, distillation, column chromatography, liquid chromatography, recrystallization and the like in combination.

The peptide of the present invention is preferably a cyclic peptide, particularly preferably a cyclic peptide containing a Cys-Cys disulfide bond. The cyclic peptide of the present invention can be produced by using a known method for producing a cyclic peptide. Examples thereof include, but are not limited to, a method of attaining cyclization by forming a cross-link utilizing a disulfide bond between two Cys residues, a method of attaining cyclization by forming an intramolecular cross-link utilizing olefin metathesis, a method of attaining cyclization by mutually crosslinking side-chain functional groups of amino acid residues, a method of attaining cyclization by forming a cyclic thioether between cysteine residues, and the Like.

One embodiment of the peptide of the present invention is a cyclic peptide containing one sequence selected from the above-described sequences, as the sequence in its cycle. The number of amino acids in the cycle is not particularly restricted, and is preferably 5 to 15, more preferably b to 9 including the above-described sequences and excluding amino acids forming a cross-link.

The cell membrane-permeable peptide of the present invention containing a Cys-Cys disulfide bond is, for example, a peptide containing an amino acid sequence containing one sequence selected from the above-described sequences as the internal sequence in the cycle, further containing first Cys located outside the N-terminal direction of the internal sequence and second Cys located outside the C-terminal direction of the internal sequence, and in which these Cys sequences mutually form a disulfide bond to give a cyclic peptide, but the peptide is not limited to this.

(2) Biologically Active Substance

In the present invention, the term biologically active substance (hereinafter, simply referred to as an active substance in some cases) has a meaning including both a low molecular compound and a high molecular substance showing a biological activity when administered to a biological body.

The above-described low molecular compound includes, but is not limited to, low molecular compounds contained as an active ingredient in a medicinal product used for treatment and/or prevention of various diseases or low molecular compounds having various biological activities.

The above-described high molecular substance includes, but is not limited to, for example, a protein, a peptide, nucleic acids, and analogs thereof.

The protein includes proteins having a biological activity, and includes proteins and the like used for treatment and/or prevention of diseases. Examples thereof include, but are not limited to, an enzyme, an antibody, a transcription factor, or specific portions constituting them. Specifically, albumins and antibodies are mentioned.

The above-described peptide includes biologically active peptides, and includes peptides and the like used for treatment and/or prevention of diseases. Specific examples thereof include, but are not limited to, insulin, glucagon-like peptide-1 and derivatives thereof for diabetes therapy.

The above-described nucleic acids includes nucleic acids used for treatment and/or prevention of diseases. Examples thereof include antisense DNA and siRNA and shRNA for treatment of various diseases by a gene knockdown method using antisense DNA and RNA interference. Specific examples thereof include, but are not limited to, NF-kb-targeted siRNA for fulminant hepatitis and transthyretin-targeted siRNA and antisense DNA for familial amyloid angiopathy.

Examples of the drug which can be suitably used as a biologically active substance in the composition of the present invention include, but are not limited to, for example, peptide/protein medicinal products such as insulin and insulin secretion promoters, and, steroid hormones, non-steroidal anti-inflammatory agents, antihistamine agents, anti-allergic drugs, anti-asthmatic drugs, antiparkinsonian drugs, antidementia drugs, psychotropic drugs, antihypertensive drugs, cardiac disease curative drugs, circulation organ improving drugs, antiemetic drugs, diuretic agents, antithrombogenic drugs and antineoplastic drugs. Since the cell membrane-permeable peptide of the present invention promotes permeation in small intestine, a substance showing more effective drug efficacy based on promotion of absorption from the digestive tract is within the range of the subject of the present invention.

In the composition of the present invention, the cell membrane-permeable peptide of the present invention may be bonded to these active substances, alternatively, a composite may be formed between the peptide and these active substances. The bond of the peptide to the active substance (for example, covalent bond or non-covalent bond-like mutual interaction) can be attained by a known method, and the method can be selected appropriately depending on the kind of the active substance to be used. For example, the peptide of the present invention can be bonded directly or via a linker to the terminal of nucleic acids or a biologically active peptide as the active substance, and the technology of bonding a short peptide to a peptide or nucleic acids can be performed using a known method. Formation of a composite of the peptide and the active substance can also be conducted by a known method, and the method can be selected appropriately depending on the kind of the active substance to be used.

(3) Active Substance Carrier

The active substance carrier in the composition of the present invention includes carriers capable of bonding to the above-described active substance or in which the above-described active substance can be placed. The active substance includes, but is not limited to, for example, liposomes, cyclodextrins and derivatives thereof, nanoparticles and micelles. The means for incorporating the active substance in such a carrier are known, and these known methods can be used in the present invention. Also various carriers, including production methods and acquisition channels thereof, are known and these can be used.

The carrier which can promote absorption in the digestive tract by adding the cell membrane-permeable peptide of the present invention includes, but is not limited to, for example, liposomes and cyclodextrins.

In the composition of the present invention, the cell membrane-permeable peptide of the present invention may be bonded to an active substance carrier (for example, liposome and cyclodextrin) containing the biologically active substances, alternatively, a composite may be formed between the peptide and the carrier containing the active substances. The bond of the peptide to the carrier (for example, covalent bond or non-covalent bond-like mutual interaction) can be attained by a known method, and the method can be selected appropriately depending on the kind of the carrier to be used. Formation of a composite of the peptide and the carrier can also be conducted by a known method, and the method can be selected appropriately depending on the kind of the active substance to be used. For example, in the case of a composite with a liposome, a fatty acid can be added to the C-terminal of the cell membrane-permeable peptide of the present invention, to cause insertion into the liposome membrane (see, WO2013/140643). In addition, the cell membrane-permeable peptide of the present invention can be bonded to and presented on the surface of a liposome and a cyclodextrin which can enclose an active substance, by using a known method.

As described above, it is possible to make, for example, a highly versatile intestine-permeable drug delivery system.

(4) Composition

The cell membrane-permeable peptide of the present invention does not contain arginine as a basic amino acid at all or, if any, contains a single base, in the 5 to 7-amino acid sequence portion described above. For this reason, the peptide has characteristics of excellent solubility in water and easy solubilization. Thus, the cell membrane-permeable peptide of the present invention has high applicability to various active substances, and the composition of the present invention can be easily prepared.

Further, the cell membrane-permeable peptide of the present invention can transport an extremely large molecule called M13 phage. Therefore, the composition of the present invention is excellent in transportation of a large active substance.

The composition of the present invention can be utilized as a medicine. The medicinal product containing the composition of the present invention can be formulated into a preparation according to a known method, and the preparation can be administered. For example, the preparation can be orally or parenterally administered, in the form of a liquid preparation or in the form of a medicinal composition having suitable formulation, to mammals including human, and the medicinal composition containing the composition of the present invention is preferably administered orally.

In the medicinal composition containing the composition of the present invention, optional ingredients can be blended appropriately not as long as deteriorating the effect of the active substance and the cell membrane-permeable peptide of the present invention. The optional ingredient includes, but is not limited to, for example, a cross-linking agent, a solubilizing agent, an emulsifying agent, a moisturizing agent, a refreshing agent, an inorganic powder, an antioxidizing agent, an antiseptic agent, a coloring agent, a flavoring agent, a pH adjusting agent and a stabilizing agent.

The dosage amount of the composition of the present invention to human is determined appropriately depending on the kind of the active substance contained, the age, the body weight, the condition, the sex of the administration subject, the administration method, and other conditions. For example, the administration amount of the active substance is about 0.01 mg/kg to about 10 mg/kg per day.

EXAMPLES

The present invention will be illustrated below referring to examples, but the present invention is not limited to the examples described below.

(Example 1) Screening of Human Small Intestine Permeable Peptide

To identify a cyclic peptide capable of transporting a high molecular medicinal product which efficiently permeates small intestine as the main tissue of digestive tract absorption, screening of human small intestine permeable peptides was carried out.

For identification of cyclic peptides, a phage library ($1 \times 10^9$ kinds) in which 7 amino acids are presented randomly and Caco-2 cells generally used as the human small intestine model cell were used.

(1) Production of Phage Library

Ph.D. (registered trademark)—C7C Phage Display Peptide Library Kit (manufactured by BioLab) was purchased, and a phage library was obtained. The cyclic amino acid structure displayed in a phage is shown in FIG. 1.

(2) Screening of Permeable Peptide

The experiment of permeation using Caco-2 cells was conducted according to a report of Ohura et al. (J. Pharm. Sci. Vol 100, No. 9, 2011). Each phage stock was prepared by diluting with an HBSS buffer so as to give a concentration of $5 \times 10^{11}$ pfu/mL. Caco-2 cells placed in Transwell (manufactured by Coring) were cultured, and formation of sufficient tight junction was confirmed, then, Transwell was transferred to a new 6-well plate. To the apical (AP) side of the cell, 2 mL of the phage preparation liquid was added and incubated at 37° C. (this time point t=0 min). When reached each time point, Transwell was transferred to a new 6-well plate. The time point was 1, 3, 5, 10 and 30 min. The sample at the basal (BA) side at each time point was kept on ice. When reached 30 min, Transwell was transferred to a new 6-well plate, and the HBSS buffer at the AP side was aspirated, then, the cells were recovered into a centrifugal tube. The titre at the BA side and the titre in the supernatant at each time point were measured by qPCR.

Recovering and proliferation over time of phages permeated to the BA side as described above were repeated three times in total, and phages presenting peptides permeating Caco-2 cells were selected. As a result of carrying out DNA sequence analysis for identifying peptides presented by phages which permeated Caco-2 cells, 49 kinds of cyclic peptides were identified. Of the identified 49 kinds of the amino acid sequences composed of 7 amino acids, 45 kinds of the sequences detected only once, while 4 amino acid sequences described in Table 1 below exhibited an appearance frequency of 2 or 3 in three experiments.

TABLE 1

| Peptide Name | Sequence | Appearance Frequency |
|---|---|---|
| D N P | D N P G N E T (SEQ ID No: 5) | 3 |
| T V S | T V S R P A F (SEQ ID No: 6) | 3 |
| H S N | H S N D P R N (SEQ ID No: 7) | 3 |
| P F M | P F M S V A N (SEQ ID No: 8) | 2 |

(Example 2) Permeability of Identified Amino Acid Sequence Peptide

Figure 2:
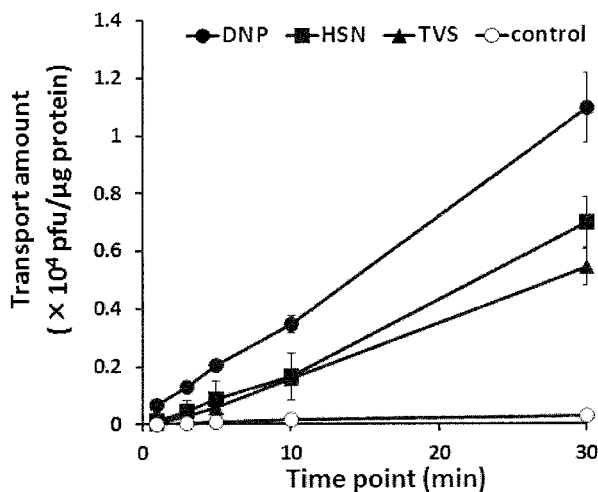
FIG. 2 shows the results of permeability of phages presenting peptides comprising a 7-amino acid sequence screened, using Caco-2 cells.

The above-described identified three peptides (peptide: DNP, HSN, TVS) exhibiting an appearance frequency of 3 were selected and the transportation properties of respective peptide presenting phages were analyzed to find that they permeated Caco-2 cells over time and the permeation amounts until 30 minutes were 39 times, 26 times and 21 times higher as compared with a peptide non-presenting phage (control). The results are shown in FIG. 2.

Using the cyclic peptide DNP as a peptide showing highest permeation activity, influences on cell toxicity to Caco-2 cells and tight junction thereof were confirmed.

For cell toxicity, 100 µL of 0-10 µM DNP peptide was added to Caco-2 cells cultured in a 96-well plate, and the cell survival rates after 1, 6 and 24 hours were measured using Cell Counting kit 8 (DOJINDO Laboratories).

For the influence on tight junction, Caco-2 cells were cultured in Transwell, then, 2 mL of 0-10 µM peptide DNP was added at the apical (AP) side, and 1, 2, 3, 6, 12 and 24 hours after addition, the electric resistance value (TEER) was measured using Millicell ERS-2.

Caco-2 cells were treated for 24 hours using the cyclic peptide DNP having highest permeability at a concentration of 10 µM, but weakening of cell toxicity and tight junction was not observed. The permeation route includes a transcellular route by which a material permeates in a cell and a paracellular route by which a material passes through between cells, and the above-described results suggested that this identified cyclic peptide permeates in a cell and causes low cell damage.

(Example 3) Confirmation of Small Intestine Permeability in Mouse

Small intestine permeability of the cyclic peptide screened in Example 1 was analyzed as described below by an in situ closed loop method using a digestive tract loop of an ICR mouse.

Respective peptide-presenting phages $1.0 \times 10^{11}$ pfu (in 1 m LHBSS buffer) of the three peptides (peptide: DNP, HSN, TVS) were injected from a cannula. This time point is 0 min. Then, at 10, 20 and 30 min, blood was collected each in an amount of 100 µL from tervical vein, and the titre in blood was measured by a plaque count method. As the control, a peptide-non-presenting phage (control) was used.

Figure 3:
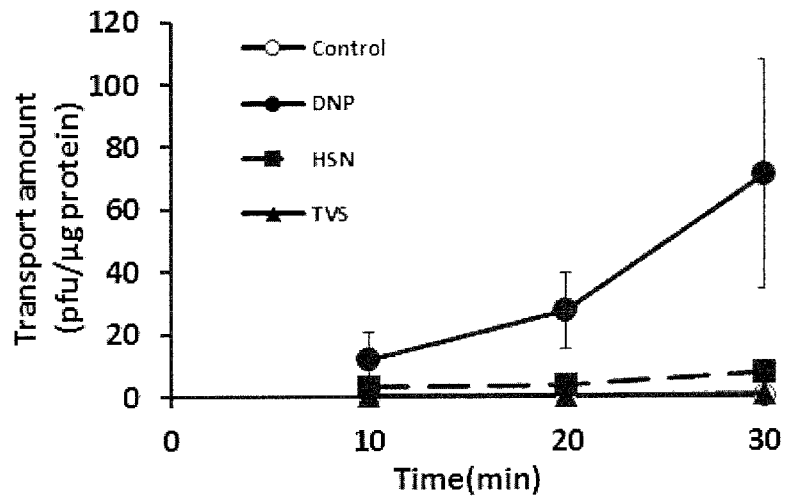
FIG. 3 shows the results of small intestine permeability of cyclic peptides screened, by an in situ closed loop method using a digestive tract loop of an ICR mouse.

The results are shown in FIG. 3. The cyclic peptides DNP, HSN and TVS-presenting phages permeated mouse small intestine over time, and 30 minutes after administration, the phage concentrations in plasma were 1271 times, 138 times and 17 times higher than the concentration of the control.

From the above-described results, cyclic peptides having small intestine permeability were identified. M13 phage (about 16 MDa) used in the above-described experiments is a macromolecule and permeation of this with the aid of the cell membrane-permeable peptide of the present invention succeeded, thus, the cell membrane-permeable peptide of the present invention can be applied to promotion of absorption in the digestive tract of a high molecular medicinal product and a liposome.

(Example 4) Competitive Inhibition of Synthetic Peptide

Figure 4:
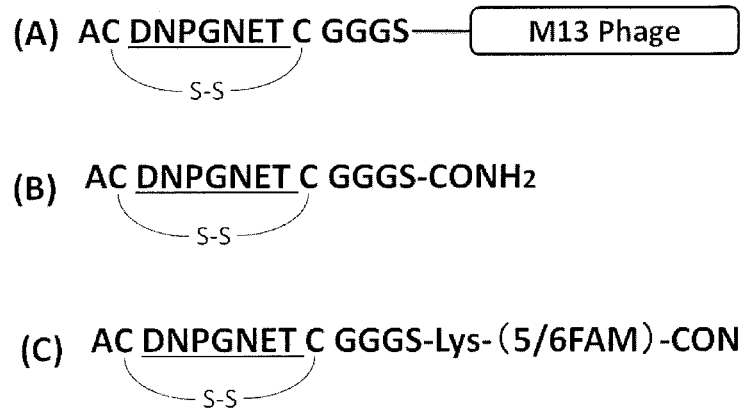
FIG. 4 is a view showing the amino acid sequences and the structures of synthesized peptides. (A) shows the structure of a DNP-presenting M13 phage, (B) shows a synthetic unlabeled DNP peptide and (C) shows a synthetic FAM-labeled DNP peptide.

We asked Scrum Inc. to synthesize a cyclic peptide having an amino acid sequence which is the same as the amino acid sequence portion of the cyclic peptide DNP-presenting phage ("called unlabeled DNP peptide"), and a FAM-labeled DNP peptide carrying a fluorescent pigment bonded to the C-terminal thereof via Lys. The respective structures are shown in FIGS. 4B and 4C. FIG. 4A shows the structure of the DNP-presenting M13 phage.

Figure 5:
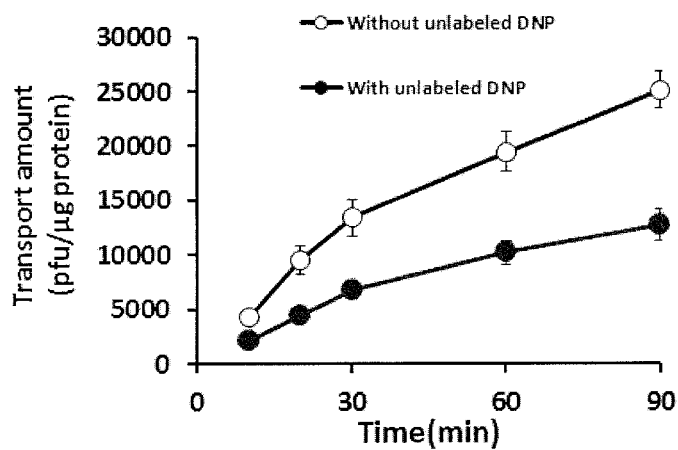
FIG. 5 shows the results of measurement of a DNP-presenting phage permeating Caco-2 cells in the presence or in the absence of unlabeled DNP.

The DNP-presenting phage permeating Caco-2 cells was measured in the presence or in the absence of the unlabeled DNP, in the same manner as in Example 1. The concentration of the unlabeled DNP used is 10 µM. The results are shown in FIG. 5. It was confirmed that competitive inhibition occurs by the synthetic unlabeled DNP peptide.

Figure 6:
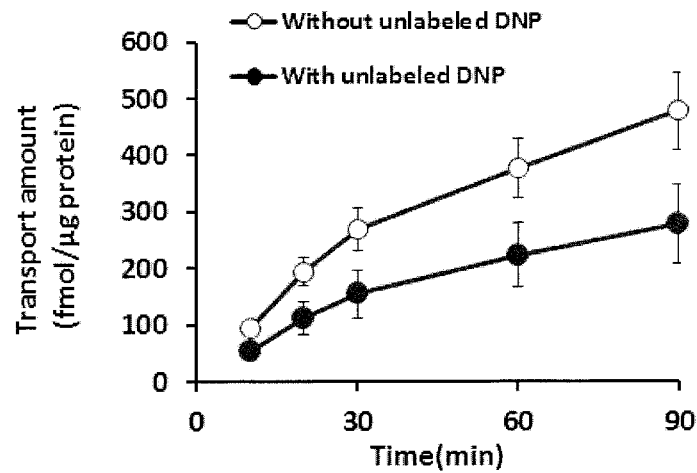
FIG. 6 shows the results of measurement of a FAM-labeled DNP peptide permeating Caco-2 cells in the presence or in the absence of unlabeled DNP.

Then, the FAM-labeled DNP peptide permeating Caco-2 cells was measured in the presence or in the absence of the unlabeled DNP, in the same manner as for the permeation experiment of Caco-2 cells used in Example 1. The concentration of the unlabeled DNP used was 10 µM, and the concentration of the FAM-labeled DNP was 10 µM. The results are shown in FIG. 6.

(Example 5) Permeability of Synthetic Peptide in Mouse Small Intestine

Using the FAM-labeled DNP peptide synthesized, small intestine permeability in a mouse was measured in the same manner as in Example 3. The results are shown in FIG. 7. It was confirmed that the synthetic FAM-labeled DNP peptide permeated small intestine of a mouse over time and the plasma concentration thereof increased over time.

(Example 6) Alignment Analysis of 4 Peptides Identified

The amino acid sequences of the four peptides identified in Example 1 were alignment-analyzed using the M-Coffe web server (Moretti et al., Nucleic Acids Research, 2007, vol. 35, Web Server Issue W645-648). The results are shown in FIG. 8. Surrounded by a solid line frame are amino acids of which consistency was GOOD as the result of the alignment analysis. Extremely high consistency scores are shown between four sequences.

(Example 7) Confirmation of Promotion of Insulin Absorption by Co-Administration of Cyclic Peptide The influence on insulin absorption by co-administration of the cyclic peptide of the present invention was studied by measuring the blood glucose level.

We asked GenScript Japan Inc. to synthesize a cyclic peptide shown in FIG. 4B containing a sequence of DNPG-NET (SEQ TD No: 5).

A peptide was prepared by using 100 µL of a hot HBSS solution so that the concentration of insulin was 10 IU/kg and the concentration of DNPGNET was 5 mM and incubated at 37° C. for 1 hour, and the resultant was used in the co-administration group. For the insulin single administration group, a sample was prepared by using 100 µL of a hot HBSS solution so that the concentration of insulin was 10 IU/kg and incubated at 37° C. for 1 hour, and the resultant peptide was used. In the same manner as in Example 6, a mouse small intestine closed loop was produced, then, the DNPGNET+insulin solution or the insulin solution prepared previously was administered into the loop. The time of administration was 0 min, and the blood glucose level was measured over a time of 60 minutes by using ACCU-CHEK (registered trademark) Aviva Nano. The results are shown in FIG. 9. It was confirmed that absorption of insulin was promoted by co-administration of the peptide of the present invention.

The above-described detailed description merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The cell membrane-permeable peptide of the present invention can be applied to a high molecular medicinal product and is useful as a permeable peptide. The cell membrane-permeable peptide of the present invention can be further applied to promote absorption in the digestive tract of a high molecular medicinal product and a liposome, and is useful as a high molecular medicinal product efficiently permeating small intestine as the main tissue of digestive tract absorption.

SEQUENCE LISTING

The invention claimed is:

1. A cell membrane-permeable cyclic peptide comprising an amino acid sequence selected from the group consisting of amino acid sequences: DNPGN (SEQ ID No: 1), SRPAF (SEQ ID No: 2), NDPRN (SEQ ID No: 3) and MSVAN (SEQ ID No: 4) in its cycle, wherein the number of amino acids in the cycle is 5 to 15, provided that the number of amino acids in the cycle excludes amino acids forming a cross-link.

2. The cell membrane-permeable cyclic peptide according to claim 1, wherein the cyclic peptide comprises at least one unnatural amino acid.

3. The cell membrane-permeable cyclic peptide according to claim 1, wherein the cyclic peptide comprising an amino acid sequence selected from the group consisting of amino acid sequences: DNPGNET (SEQ ID No: 5), TVSRPAF (SEQ ID No: 6), HSNDPRN (SEQ ID No: 7) and PFMSVAN (SEQ ID No: 8).

4. The cell membrane-permeable cyclic peptide according to claim 1, wherein the amino acid sequence is DNPGN (SEQ ID No: 1) or DNPGNE (SEQ ID No: 9).

5. The cell membrane-permeable cyclic peptide according to claim 1, wherein the cyclic peptide contains a Cys-Cys disulfide bond.

6. The cell membrane-permeable cyclic peptide according to claim 1, wherein the cyclic peptide permeates small intestine epithelial cells of mammals.

7. A cell membrane-permeable composition, comprising:
a cyclic peptide comprising an amino acid sequence selected from the group consisting of amino acid sequences: DNPGN (SEQ ID No: 1), SRPAF (SEQ ID No: 2), NDPRN (SEQ ID No: 3) and MSVAN (SEQ ID No: 4) in its cycle, wherein a number of amino acids in the cycle is 5 to 15, providing provided that the number of the amino acids in the cycle excludes amino acids forming a cross-link, and
a biologically active substance,
wherein the cyclic peptide binds to or forms a complex with the biologically active substance or an active substance carrier containing the biologically active substance.

8. The composition according to claim 7, wherein the cyclic peptide comprises at least one unnatural amino acid.

9. The composition according to claim 7, wherein the cyclic peptide comprises an amino acid sequence selected from the group consisting of amino acid sequences: DNPGNET (SEQ ID No: 5), TVSRPAF (SEQ ID No: 6), HSNDPRN (SEQ ID No: 7) and PFMSVAN (SEQ ID No: 8).

10. The corn position according to claim 7, wherein the amino acid sequences is DNPGN (SEQ ID No: 1) or DNPGNE (SEQ ID No: 9).

11. The composition according to claim 7, wherein the cyclic peptide contains a Cys-Cys disulfide bond.

12. The composition according to claim 7, wherein the biologically active substance is a protein.

13. The composition according to claim 7, wherein the biologically active substance is a biologically active peptide.

14. The composition according to claim 13, wherein the biologically active peptide is insulin.

15. The composition according to claim 7, wherein the biologically active substance is at least one nucleic acid.

16. The composition according to claim 15, wherein the at least one nucleic acid is antisense DNA, siRNA or shRNA.

17. The composition according to claim 7, wherein the active substance carrier containing the biologically active substance is a liposome.

18. The composition according to claim 7, wherein the active substance carrier containing the biologically active substance is a cyclodextrin.

* * * * *